United States Patent [19]

Johnson

[11] Patent Number: 4,943,396
[45] Date of Patent: Jul. 24, 1990

[54] PROCESS FOR PREPARING LINEAR ALPHA, OMEGA DIFUNCTIONAL MOLECULES

[75] Inventor: Thomas H. Johnson, Houston, Tex.

[73] Assignee: Shell Oil Company, Houston, Tex.

[21] Appl. No.: 247,476

[22] Filed: Sep. 22, 1988

[51] Int. Cl.$^5$ .............................. C09F 5/00; C09F 5/08
[52] U.S. Cl. .............................. 260/405.5; 260/405.6; 260/410.9 R; 260/413; 558/265; 560/190; 560/203; 560/262; 560/302; 568/564; 568/673; 568/857
[58] Field of Search .......... 260/405.5, 405.6, 410.9 R, 260/413; 558/265; 568/673, 857, 564; 560/190, 203, 262, 302

[56] References Cited

U.S. PATENT DOCUMENTS

| | | | |
|---|---|---|---|
| 3,865,868 | 2/1975 | Lewis | 260/475 N |
| 4,269,780 | 5/1981 | Banasiak | 260/405 |
| 4,371,469 | 2/1983 | Foglia et al. | 260/405.6 |
| 4,480,049 | 10/1984 | Johnson | 502/231 |
| 4,489,171 | 12/1984 | Johnson | 502/231 |
| 4,550,216 | 10/1985 | Basset et al. | 585/645 |
| 4,560,792 | 12/1985 | Banasiak | 560/261 |
| 4,654,462 | 3/1987 | Basset et al. | 585/646 |
| 4,681,956 | 7/1987 | Shrock | 556/12 |
| 4,727,215 | 2/1988 | Shrock | 585/645 |

OTHER PUBLICATIONS

J. of the Amer. Oil Chemist's Society, vol. 51, 1974, pp. 381–384.
Tetrahedron Letters, No. 5, 1977, pp. 441–442.
J. of the Amer. Oil Chemist's Society, vol. 56, 1979, pp. 823A–826A.
J. of Organometallic Chemistry, 255, 1983, pp. 159–171.
J. of the Amer. Oil Chemist's Society, vol. 65, 1985, pp. 888–891.

*Primary Examiner*—Paul J. Killos

[57] ABSTRACT

The present invention relates to a process for preparing linear alpha, omega difunctional molecules by a process which comprises isomerizing olefins having at least one terminal functional group to form a mixture of functionalized olefinic isomers and metathesizing said functionalized olefinic isomers to produce a mixture of difunctional molecules and internal olefins.

5 Claims, No Drawings

PROCESS FOR PREPARING LINEAR ALPHA, OMEGA DIFUNCTIONAL MOLECULES

FIELD OF THE INVENTION

This invention relates to a process for preparing linear alpha, omega difunctional molecules by the isomerization and metathesis of an olefin having at least one terminal functional group.

BACKGROUND OF THE INVENTION

The synthesis of linear alpha, omega difunctional molecules is currently limited to a few special cases where the chemistry is specific for only a few reactants, or where the chemistry is general but the required reactants are not generally available. For example, the ring opening of tetrahydrofuran to 1,4-butanediol is a highly efficient way to make this particular alpha, omega diol. However, ring opening of higher molecular weight cyclic ethers does not proceed as well as the ring opening of tetrahydrofuran nor are cyclic ethers readily available in a wide range of carbon numbers. Therefore, the ring opening method for synthesizing alpha, omega difunctional molecules is limited to a small carbon-number range of diols. Another method for synthesizing linear alpha, omega difunctional molecules is the synthesis of adipic acid via the two step oxidation of cyclohexane. This method is limited by the lack of a wide range of other cycloalkanes. A further method for synthesizing linear alpha, omega difunctional molecules is the ethenolysis of cyclooctene to deca-1,9diene. This method is also limited by the lack of a wide range of other cycloalkenes.

All of the above methods for synthesizing linear alpha, omega difunctional molecules are very specific processes and not adaptable to synthesizing linear alpha, omega difunctional molecules other than the few difunctional molecules for which the method is specific or the reactants are readily available. There is, therefore, a need to find a general process for preparing a wide carbon-number range of linear alpha, omega difunctional molecules. The invention described herein is, therefore, directed to a general process for preparing linear alpha, omega difunctional molecules.

SUMMARY OF THE INVENTION

The present invention relates to a process for preparing linear alpha, omega ($\alpha, \omega$) difunctional molecules by a process which comprises isomerizing an olefin having at least one terminal functional group and subsequently metathesizing or disproportionating the isomers formed to produce a family of difunctional molecules and internal olefins.

DESCRIPTION OF THE PREFERRED EMBODIMENTS

The present invention provides a process for preparing linear $\alpha, \omega$ difunctional molecules by isomerizing olefins having at least one terminal functional group and then metathesizing them to a family of difunctional molecules and olefins.

The present invention deal with the isomerization and disproportionation of an olefin having at least one terminal functional group selected from groups having the formulas

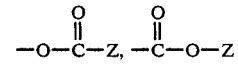

and O-Z wherein Z is a hydrocarbyl group having 1 to about 20 carbon atoms, a hydrocarbyloxy group having 1 to about 20 carbon atoms or hydrogen. Preferably, Z is a hydrocarbyl group although Z can be any substituent which does not interfere with the reaction. Thus, suitable functional olefins include alkylene acid esters, alkylene esters, alkylene ethers, alkylene anhydrides, alkylene carbonates, dialkylene alkyl glycerides, alkylene dialkyl glycerides and trialkylene glycerides. The preferred functional olefins are those wherein the olefinic hydrocarbyl portion thereof has the formula $Z'-CH=CH(CH_2)_n$ wherein n is in the range of 2 to 20 and $Z'$ is hydrogen or alkyl radical having 1 to 20 carbon atoms. It is also within scope of the present invention to use a functional olefin having two terminal functional groups of the types described above. It is further within the scope of the present invention to use a monoolefin or a polyolefin having at least one terminal functional group. Typically, the preferred functional olefins contain no more than about 30 carbon atoms per molecule. Suitable functional olefins for use in the process of the instant invention include methyl oleate, oleyl acetate, methyl non-8-enoate, ethyl dec-9-enoate and the like.

The isomerization procedure can be effected in any suitable manner and may comprise either a batch or a continuous type operation. The preferred method by which the process of this invention ma be effected is a continuous type operation. One particular method is the fixed bed operation in which the isomerizable olefin is continuously charged to a reaction zone containing a fixed bed of the desired catalyst, said zone being maintained at isomerization conditions, including a gas or liquid phase and at a temperature in the rang of from about 0° C. to about 500° C., a pressure in the range of from about 1.0 psig to about 2000 psig and a weight hourly space velocity in the rang of from about 0.1 to about 20. The preferred isomerization conditions include a temperature in the range of from about 100° C. to about 275° C., a pressure in the range of from about 14 psig to about 1000 psig and a weight hourly space velocity in the range of from about 0.1 to about 20. The isomerization reaction is usually carried out in a liquid phase and if desired liquid reaction diluents are utilized. Examples of suitable diluents include hydrocarbons free from aliphatic unsaturation, such as acyclic or alicyclic alkanes of from about 6 to about 12 carbon atoms, i.e., hexane, isooctane, and cyclohexane. If a diluent is added, it is present in an amount of about 100 moles of diluent per mole of olefinic reactants, preferably about 20 moles of diluent per mole of reactant.

The olefins are isomerized in the presence of an isomerization catalyst which causes little or no branching. Further, it is desirable to have an isomerization catalyst which can be controlled such that varying degrees of isomerization can take place. In this manner, the carbon-number distribution of the difunctional molecules can be controlled. Preferred catalysts are those which have little or no polymerization, branching or cracking activity. Some examples of suitable isomerization catalysts include alumina supported palladium, silica supported palladium, tantalum halide/oxide-metal oxide (U.S. Pat. No. 4,489,171, the teachings of which are incorporated by reference herein), niobium halide/oxide-metal oxide (U.S. Pat. No. 4,480,049, the teachings of which are incorporated by reference herein) and the like.

The isomerization reaction zone may comprise an unpacked vessel or a vessel containing a fixed catalyst bed. The charge passes through the catalyst bed in either an upward or downward flow and the isomerized product is continuously withdrawn, separated from the reactor effluent, and recovered by conventional means, while any unreacted starting materials may be recycled to form a portion of the feedstock. It is also contemplated as being within the scope of this invention that reaction gases such as hydrogen, nitrogen, argon, etc., can be charged to the reaction zone if desired. A second continuous type operation comprises the moving bed type in which the isomerizable olefin and the catalyst bed move either concurrently or countercurrently to each other while passing through said reaction zone. In a third continuous type operation, the isomerizable olefin can also be passed through a fluidized bed of catalyst particles.

Another type of operation which may be used is the batch type operation in which a quantity of the isomerizable olefin and the catalyst are placed in an appropriate apparatus such as, for example, a rotating or stirred autoclave. The apparatus is then heated to the desired temperature and pressure and maintained at that temperature and pressure for a predetermined residence time at the end of which the flask and contents thereof are cooled to room temperature and the desired reaction product is recovered by conventional means, such as, for example, by washing, drying, fractional distillation, crystallization, etc.

The isomerization procedure yields a product mixture in which the double bond has been isomerized to various points along the carbon backbone to various degrees depending on the isomerization conditions. These isomerization products may be used for applications such as ozonolysis, epoxidation and the preparation of dimer acids, or, they may be subjected to further processes, such as metathesis in order to form other useful products such as diesters and internal olefins.

In the instant invention, the isomerized functionalized olefins are subjected to metathesis or disproportionation in order to form linear alpha, omega difunctional molecules comprising a mixture of difunctional molecules and internal olefins. The disproportation of olefins containing other functional groups is a very desirable technique for obtaining valuable chemicals that otherwise would require multistep preparations that are costly and often give products that are difficult to purify. The metathesis of olefins containing ester and ether groups is particularly interesting in that it provides a route to chemicals having many potential applications.

The metathesis of functionalized olefins is well known to be more difficult than the metathesis of non-functionalized olefins. Many olefin metathesis catalysts are not active with functionalized olefin substrates and those that are active often give low conversions and/or low rates of reaction. The catalyst system used in the metathesis of functionalized olefins can be either a homogeneous or a heterogeneous catalyst system. Tungsten-based catalysts which are suitable for use in the instant process are discussed in Baker et al, Tetrahedron Letters, p. 441 (1977). Rhenium-based catalysts which are suitable for the metathesis of functionalized olefins are discussed in R.H.A. Bosma et al, Journal of Organometallic Chemistry, Vol. 255 (1983) pp. 159–171. Examples of catalyst systems which are suitable for metathesizing functionalized olefins include $WCl_6/Me_4Sn$ and $Re_2O_7/Al_2O_3-R_4Sn$ wherein R is an alkyl group. Catalyst systems particularly preferred in the instant invention include $WCl_6/Me_4Sn$ and $Re_2O_7/Al_2O_3-Me_4Sn$. In a preferred embodiment, the catalyst system additionally contains an oxophilic agent to increase the rate of metathesis. Oxophilic agents suitable for use in the catalyst system are metal-containing compounds wherein the metal used has a metal-oxygen bond strength greater than the metal-oxygen bond strength of the metathesis transition metal, i.e., tungsten and rhenium, utilized in the metathesis catalyst. Typically, the oxophilic agent is a compound having the formula M-X wherein M is zirconium, samarium, lanthanum, and the like, or any other metal having a metal-oxygen bond strength greater than the bond strength of the metathesis metal and X comprises one or more organic or inorganic species which in combination neutralize the charge of M. Examples of suitable species for X include sulfate, phosphate, cyclopentadienyl, and the like.

The metathesis of the functionalized olefins can be carried out either batchwise or continuously, using a fixed catalyst bed, or a stirrer equipped reactor or other mobile catalyst contacting process as well as any other well known contacting technique. Preferred reaction conditions, e.g., temperature, pressure, flow rates, etc., vary somewhat depending upon the specific catalyst composition, the particular feed olefin, desired products, etc. The process is carried out at temperatures ranging from about 0° C. to about 350° C., preferably from about 0° C. to about 200° C., and at pressures in the range of from 14 psig to about 1000 psig, preferably from about 14 psig to about 500 psig. The metathesis reaction is usually effected in a liquid phase and if desired, liquid reaction diluents are utilized. Examples of suitable diluents are hydrocarbons free from aliphatic unsaturation, such as acyclic or alicyclic alkanes of from about 6 to about 12 carbon atoms, i.e. hexane, isooctane and cyclohexane. Also exemplary would be monoaromatic compounds such as benzene, chlorobenzene and toluene. If the diluent is added, it is present in an amount of about 100 moles of diluent per mole of olefinic reactants, preferably about 20 moles of diluent per mole of olefinic reactant.

The presence of molecular oxygen and water has been found to be deleterious to the metathesis reaction and should be substantially avoided during the reaction. Inert gases such as nitrogen argon or helium can be used to maintain a dry inert atmosphere during the reaction.

In the metathesis reaction a purification step to remove impurities such as, for example, hydroperoxides and residual alcohols or acids, by such methods as filtering through silica gel or alumina and storing over molecular sieves or distilling from suitable drying agents is beneficial.

The operable range of contact time for the process of this invention depends primarily upon the operating temperature and the activity of the catalyst, which is influenced by surface area if the catalyst is heterogeneous, promoter concentration, activation temperature, etc. Suitable combinations of contact time and temperature can be selected to alter the distribution of products as desired. With proper selection of conditions and contact times, very high efficiency of conversion of desired products can be obtained.

With a fixed bed reactor, continuous flow operation typically is conducted at pressures in the range of from about 1.0 psig to about 2000 psig, preferably from about 50 psig to about 500 psig, and at temperatures in the range of from about 0° C. to about 500° C., preferably about 100° C. to about 250° C., with weight hourly space velocities in the range of from about 0.1 to about 20.0 parts by weight of olefinic feed per part by weight of catalyst per hour. The space velocity is adjusted according to the presence of inert diluents, changes in density of feed due to change of pressure or temperature, and variation in reaction temperature and the activity of the catalyst. The higher space velocities in general are associated with higher reaction temperatures.

The isomerization and subsequent metathesis of functionalized olefins results in the production of linear alpha, omega difunctional molecules comprising a mixture of difunctional molecules and internal olefins. The difunctional molecules prepared according to the invention are useful as adhesives and crosslinking agents in the conversion of polymers to elastomeric materials.

In a preferred embodiment, methyl oleate is contacted at isomerization conditions, i.e., a temperature in the range between about 100° C. and about 275° C, and a pressure in the range between about 50 psig and about 1000 psig, with an isomerization catalyst to form a mixture of octadecenoates. The octadecenoate isomers are then contacted at metathesis conditions, i.e., a temperature in the range between about 0° C. and about 200° C. and a pressure in the range between about 14 psig and about 1000 psig, with a metathesis catalyst to form a mixture of alkene dioates and alkenes.

The process of the instant invention will be further described below by the following example which are illustrative and which are not be construed as limiting the scope of the invention.

EXAMPLE

A. Fixed Bed Isomerization of Methyl Oleate

Methyl oleate feed was fed upflow through a fixed-bed flow reactor (15.5"×0.62" ID) containing 20 cc of catalyst (Table 1). The pressure was maintained at 150 psi. Palladium-based catalysts were first reduced with hydrogen at 343° C. with a flow rate of 111/min for 1.5 hours. The system was then cooled and flushed with nitrogen. The results are presented in Table I.

B. Procedures for Metathesizing Methyl Oleate

The metathesis reaction was loaded and run in a Vacuum Atmospheres dry box. The chlorobenzene (Aldrich, HPLC) and olefins were purged with nitrogen for several hours and stored in the dry box. The methyl oleate (Aldrich, Tech) was vacuum distilled using a 3" ID Oldershaw column with 20 plates and operated at a 2:1 reflux ratio. Material boiling between 662-683° F.(ca 60%) was used as "methyl oleate" feed. Analysis by GC/MS showed the feed to typically be 95-97% methyl oleate containing the following impurities: methyl stearate, methyl palmitoleate, methyl palmate, and methyl myristate. GC analysis of the metathesis reactions were performed using a 60 meter × 0.2 mm ID fused silica capillary column operated at 150° C. for 4 minutes and then temperature programmed at a rate of 15° C./minute to 300° C. was obtained and held there for 30 minutes. A split ratio of 10:1 was employed.

To a 250 ml Erlenmeyer flask equipped with a magnetic stirrer, Claisen adapter, thermometer, and loose stopper (CAUTION: the stopper is loosely position to allow for a release of pressure should any build up) were added 150 ml of chlorobenzene, O.52g (1.25 mmol) of $WCl_6$ and 0.2 ml (1.5 mmol) of $Me_4Sn$. This solution was stirred for 30 minutes at 60° C., and then 3.25 g (12.5 mmol) of isomerized octadecenoates was added. The reaction was stirred at 60° C. Samples were taken for analysis at 1,4, and 19 hours. Analysis for the disappearance of methyl oleate or octadecene was performed by GC as described above. The results are presented in Table II.

TABLE I

ISOMERIZATION OF METHYL OLEATE

| Entry | Catalyst | Temp. °C. | LHSV, H-1 | Methyl Oleate, wt. % | Octadec-[a] eneoate, wt. % | Selectivity[b] % |
|---|---|---|---|---|---|---|
| 1 | 1% Pd/Al2O3 | 200 | 1.2 | 63 | 37 | 99+ |
| 2 | 1% Pd/Al2O3 | 250 | 1.2 | 35 | 65 | 99+ |
| 3 | 1% Pd/Al2O3 | 250 | 0.3 | 6 | 94 | 99+ |
| 4 | 0.5% Pd/Al2O3 | 250 | 1.2 | 53 | 47 | 99+ |
| 5 | 0.5% Pd/Al2O3 | 250 | 0.3 | 6 | 94 | 99+ |
| 6 | SiO2-Al2O3 | 250 | 0.3 | 5 | 70 | 75 |
| 7 | TaF(O)/SiO2[c] | 250 | 1.2 | 35 | 65 | 99+ |
| 8 | TaF(O)/SiO2[c] | 250 | 0.3 | 6 | 94 | 99+ |
| 9 | None | 250 | 0.3 | 92 | 8 | 99+ |

[a]Not including methyl oleate. Determined by ozonolysis.
[b]Selectivity to linear $C_{18}$ methyl ester. Based upon hydrogenation and GC integration of methyl stearate.
[c]Catalyst described in U.S. Pat. No. 4,489,171.

TABLE II

PRODUCT DISTRIBUTION FROM THE METATHESIS OF RANDOMLY ISOMERIZED METHYL OLEATE USING $WCl_6/Me_4Sn$ CATALYST[a]

| Dimethyl Alkendioate | Normalized Area %[b] |
|---|---|
| <$C_9$ | C |
| $C_{10}$ | 2.7 |
| $C_{11}$ | 3.9 |
| $C_{12}$ | 4.4 |
| $C_{13}$ | 5.0 |
| $C_{14}$ | 7.4 |
| $C_{15}$ | 6.8 |
| $C_{16}$ | 8.9 |
| $C_{17}$ | 9.9 |
| $C_{18}$ | 9.8 |
| $C_{19}$ | 8.0 |
| $C_{20}$ | 7.0 |
| $C_{21}$ | 4.7 |
| $C_{22}$ | 5.2 |
| $C_{23}$ | 4.3 |
| $C_{24}$ | 3.8 |
| $C_{25}$ | 3.3 |
| $C_{26}$ | 2.1 |
| $C_{27}$ | 1.6 |

TABLE II-continued

PRODUCT DISTRIBUTION FROM THE METATHESIS OF RANDOMLY ISOMERIZED METHYL OLEATE USING $WCl_6/Me_4Sn$ CATALYST[a]

| Dimethyl Alkendioate | Normalized Area %[b] |
|---|---|
| $C_{27}+$ | d |

[a]Feed from entry 3, Table I. Approximately 50% conversion.
[b]Determined by GC. Product identification by MS.
[c]Product quantification hampered by overlapping olefinic products and/or solvents.

I claim:

1. A process for preparing a mixture of difunctional molecules which process comprises:

(a) contacting an olefin having at least one terminal functional group wherein said terminal functional group is selected from groups having the formulas

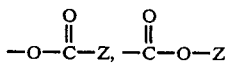

and O- wherein Z is selected from a hydrocarbyl group having from 1 to about 20 carbon atoms, a hydrocarbyl oxy group having from 1 to about 20 carbon atoms and hydrogen, at isomerization conditions with an isomerization catalyst selected from the group consisting of alumina supported palladium, silica supported palladium, tantalum halide-/oxide-metal oxide and niobium halide/oxide-metal oxide, (b) contacting the product of a) at metathesis conditions with a metathesis catalyst selected from the group consisting of $WCl_6/Me_4Sn$ and $Re_2O_7/Al_2O_3$-$R_4Sn$ wherein R is an alkyl group, and (c) recovering the product of step(b), and (d) separating difunctional molecules from the product of step c).

2. The process of claim 1 wherein said isomerization conditions include a temperature in the range of from about 0° C. to about 500° C. and a pressure in the range of from about 1.0 psig to about 2000 psig.

3. The process of claim 1 wherein said metathesis conditions include a temperature in the range of from about 0° C. to about 300° C. and a pressure in the range of from about 14 psig to about 1000 psig.

4. The process of claim 1 wherein said olefin contains about 2 to about 30 carbon atoms.

5. The process of claim 4 wherein said olefin is selected from the group consisting of methyl oleate, oleyl acetate, methyl non-8-enoate and ethyl 9 dec-9-enoate.

* * * * *